(12) United States Patent
Chen et al.

(10) Patent No.: US 7,671,233 B2
(45) Date of Patent: Mar. 2, 2010

(54) PROCESS FOR PREPARING CARBOXYLIC ACID

(75) Inventors: Chi-He Chen, Taipei (TW); Chin-Yi Lee, Taipei (TW); Chia-Jung Tsai, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 11/903,237

(22) Filed: Sep. 20, 2007

(65) Prior Publication Data

US 2008/0071110 A1    Mar. 20, 2008

(30) Foreign Application Priority Data

Sep. 20, 2006   (TW)   ............................. 95134716 A

(51) Int. Cl.
*C07C 67/36* (2006.01)
*C07C 51/12* (2006.01)

(52) U.S. Cl. ..................... 560/232; 562/519

(58) Field of Classification Search .................. None
See application file for complete search history.

(56) References Cited

U.S. PATENT DOCUMENTS

| 3,769,329 | A | 10/1973 | Paulik et al. |
| 4,690,912 | A | 9/1987 | Paulik et al. |
| 4,733,006 | A | 3/1988 | Singleton et al. |
| 5,001,259 | A | 3/1991 | Smith et al. |
| 5,442,107 | A | 8/1995 | Beevor et al. |
| 7,098,363 | B1 * | 8/2006 | Jones .................... 562/519 |

FOREIGN PATENT DOCUMENTS

| EP | 0055618 | 7/1982 |
| EP | 153834 | 9/1985 |
| WO | 9933779 | * 7/1999 |

* cited by examiner

*Primary Examiner*—Karl J Puttlitz
(74) *Attorney, Agent, or Firm*—Edwards Angell Palmer & Dodge LLP; Peter F. Corless; Dwight D. Kim

(57) ABSTRACT

A process for preparing a carboxylic acid by the carbonylation of an alcohol in a reaction medium is provided. The reaction medium includes a catalyst promoter having a metal species selected form the group consisting of group IIIA-IVA metals, group IB-VIIIB metals and lanthanides, together with a hydrohalic acid to prevent catalyst precipitation and to maintain high reaction rates in case of low water content.

20 Claims, No Drawings

PROCESS FOR PREPARING CARBOXYLIC ACID

FIELD OF THE INVENTION

The present invention relates to processes for preparing carboxylic acids, and in particular, to a process for preparing carboxylic acids by carbonylating alcohol with carbon monoxide.

BACKGROUND OF THE INVENTION

Carbonylation has been widely employed for various chemical processes, for example, synthesizing a carboxylic acid having n+1 carbon atoms by the reaction of an alcohol having n carbon atoms with carbon monoxide in the presence of catalysts.

U.S. Pat. No. 3,769,329 discloses a rhodium catalyst system for preparing acetic acid by carbonylating from methanol at relatively lower temperature and pressure, for example, at a temperature less than 300° C. and at a partial pressure of carbon monoxide lower than 15,000 psig. U.S. Pat. No. 4,690,912 further discloses that catalyst selectivity, activity and stability in carbonylation can be improved by a halogen-containing promoter component, while the carbonylation is carried out at a relatively lower temperature and pressure. Product isolation and catalyst recovery are also improved when compared to the prior art.

Although the rhodium catalyst systems taught in the above-mentioned patents can catalyze carbonylation at a lower temperature and pressure, and have the advantage of high reaction selectivity, insoluble rhodium (III) species are formed and precipitated out when methanol is carbonylated to acetic acid in the presence of rhodium catalysts at a low partial pressure and a low level of water. Therefore, the process should be operated in the presence of higher water content to maintain catalyst activity and high reaction rate. Such a high water-containing reaction system, however, can lead to large energy consumption in the subsequent purification of acetic acid.

To prevent rhodium catalyst precipitation, EP 0055618 teaches that an organic compound containing one or more nitrogen atoms, phosphorus atoms or —COOH can be added as a catalyst stabilizer. U.S. Pat. No. 4,733,006 further teaches that alkali metal acetates, such as lithium acetate, can be used as a stabilizer to overcome rhodium catalyst precipitation. Nevertheless, the relevance of a catalyst stabilizer to reaction rate of methanol carbonylation is not discussed in the aforesaid patents.

It is disclosed in U.S. Pat. No. 5,001,259 that rhodium catalyst precipitation can be improved and substantially the same reaction rate as those proceeded in high water content can be attained, when 10-20 wt % of an iodide salt of group IA metals or a group IIA metals, or a quaternary ammonium iodide is used as a rhodium catalyst stabilizer in methanol carbonylation at 1-4 wt % of water content. However, an insoluble soluble complex of rhodium with quaternary ammonium iodide (N-methylpicolinium iodide) is easily formed and precipitated from the reaction solution. As a result, the consumption of the rhodium catalyst is undesirably increased. Additionally, U.S. Pat. No. 5,001,259 indicates that high methyl acetate concentration can poison rhodium the catalyst stability even when a large amount of water is present.

Other stabilizers are described in EP153834. It discloses that thiols and imidazoles can be used as stabilizers to stabilize rhodium catalysts in the carbonylation. U.S. Pat. No. 5,442,107 further discloses that several heterocyclic nitrogen compounds are used as catalyst stabilizers in methanol carbonylation in the presence of low water content, which includes 2-ethyl-4-methylimidazole, 4-methylimidazole, 4-tert-butylpyridine, 2-hydroxylpyridine, 3-hydroxylpyridine and 4-hydroxylpyridine. However, the above-mentioned prior art fail to teach how a reaction rate is dependent on a catalyst stabilizer at low water content. Meanwhile, the disclosed catalyst stabilizers also easily react with rhodium to form insoluble complex that would precipitate from the reaction solution.

Therefore, it is desired to develop a method for preparing carboxylic acid such that a rhodium catalyst can be effectively stabilized under strict carbonylation conditions to eliminate catalyst precipitation and to keep high reaction rate, and further to reduce the energy consumption for separation and purification of acetic acid product.

SUMMARY OF THE INVENTION

It is a primary objective of the present invention to provide a process for preparing carboxylic acid that can be carried out under conditions of low water content and also prevent significant catalyst precipitation from occurrence.

It is another objective of the present invention to provide a process for preparing carboxylic acid that can be carried out under a low water content condition and maintain a high reaction rate.

To achieve the above-mentioned and other objectives, a process for preparing carboxylic acid is provided in the present invention, in which the carboxylic acid is formed by carbonylating an alcohol or its derivatives with carbon monoxide in a liquid reaction medium comprising rhodium catalyst, water, organohalide, carboxylic ester, hydrohalic acid, catalyst promoter and carboxylic acid, wherein the catalyst promoter has the structure represented by formula (I):

$$M_n Y_z \qquad (I)$$

wherein, M is selected from the group consisting of group IIIA-IVA metals, group IB-VIIIB metals and lanthanides; Y is selected from the group consisting of simple or complex anions of hydroxide, carbonate, oxalate, acetate, nitrate, oxygen-containing halic acid, sulfate, phosphate, halogen and oxygen; and n and z are integers for balancing charges. With the use of a specific catalyst promoter along with hydrohalic acid in the catalyst system of the present process, carbonylation with a high reaction rate is maintained under conditions of low water content, and catalyst precipitation in quantities is avoided.

DETAILED DESCRIPTIONS OF THE PREFERRED EMBODIMENTS

The features and efficacy of the present invention will be further described in details by referring to the following examples, but it is not meant to limit the present invention in any way.

Carboxylic acid in the present invention is produced by feeding an alcohol or its derivatives and carbon monoxide into a reactor to undergo carbonylation in the presence of a rhodium catalyst. Examples of the alcohol and its derivatives include aliphatic alcohols having 1 to 20 carbon atoms, and preferably 1 to 6 carbon atoms such as methanol, ethanol, propanol, isopropanol, isobutanol, sec-butanol, or the like; hydroxyl-containing aromatic or alicyclic compounds having 6 to 20 carbon atoms; polyols having 2 to 20 carbon atoms such as 1,3-propanediol, or 1,4-butanediol; and ether derivatives, ester derivatives thereof, or the like.

In one embodiment, methanol is used to react with carbon monoxide to obtain acetic acid via carbonylation in a reactor. The reaction medium for carbonylation carried out in the reactor contains a catalyst, for example, a rhodium catalyst; water; organohalide corresponding to the alcohol starting material, such as methyl iodide; carboxylic ester formed by reaction of the alcohol staring material with carboxylic acid, such as methyl acetate; hydrohalic acid, such as hydroiodic acid; carboxylic acid; and a catalyst promoter having the structure represented by formula (I):

$$MnYz \quad\quad\quad (I)$$

wherein, M is selected from the group consisting of group IIIA-IVA metals, group IB-VIIIB metals and lanthanides; Y is selected from the group consisting of simple or complex anions of hydroxide, carbonate, oxalate, acetate, nitrate, oxygen-containing halic acid, sulfate, phosphate, halogen and oxygen; and n and z are integers for balancing positive and negative charges. Examples of the group IIIA-IVA metals include aluminium, tin and lead, and aluminium and lead are preferred. Examples of the group IB-VIIIB metals include copper, zinc, yttrium, titanium, zirconium, vanadium, chromium, molybdenum, manganese, cobalt, nickel and palladium; and preferably copper, zinc, yttrium, zirconium, vanadium, molybdenum, manganese, cobalt and nickel. Examples of the lanthanides include, but are not limited to, lanthanum, cerium and ytterbium.

In this embodiment, methanol or methyl acetate, and acetic acid are introduced into the reactor for carbonylation together with carbon monoxide, methyl iodide, hydroiodic acid and the catalyst promoter represented by formula (I). Since esterification of methanol with carboxylic acid takes place very quickly, there is only an insignificant amount of free alcohol remained in the reactor. The outflow of the reaction products from the reactor with continuous feeding contains the target acetic acid, the corresponding methyl acetate, rhodium catalysts and halogen derivatives. The liquid reaction products are successively fed to the flash tank where acetic acid and light components are evaporated to be expelled from the top of the flash tank. Acetic acid and water are subjected to further separation in the purification section. The heavy components, including catalysts, at the bottom of the flash are managed to tank flow back to the reactor. After the obtained acetic acid is isolated in the purification section, water, a part of the acetic acid and other components (including methyl iodide, methyl acetate, and so on) are recycled to the reactor. During the period of the reaction, methyl iodide, hydroiodic acid and the catalyst promoter represented by formula (I) are continuously recycled to the reactor from the flash tank or the purification section without being consumed. To those skilled in the art, if needed, the amount of each of components in the reaction medium may be adjusted.

According to the present invention, the reaction medium for carbonylation contains generally 200 to 5000 ppm of rhodium catalyst, and preferably 500 to 2000 ppm; 1 to 14 wt % of water, and preferably 7 to 10 wt % of water; 5 to 30 wt % of organohalides, and preferably 10 to 30 wt %; 0.1 to 30 wt % of carboxylic ester, and preferably 0.1 to 5 wt %; 0.1 to 5 wt % of metal concentration of the catalyst promoter represented by formula (I), and preferably 0.5 to 2 wt %; and the rest if carboxylic acid and minor impurities. As to hydrohalic acid, it is added in an amount sufficient enough to the reaction medium to provide the reaction medium with a specific amount of halogen ions, and the undissociated hydrohalic acid is allowed to exist in the form of hydrohalic acid in the reaction medium. For example, the hydroiodic acid is usually added to the reaction medium in such an amount that more than 1 wt % of iodide anions is provided to the reaction medium, preferably more than 2.5 wt %, more preferably more than 3 wt %, and further more preferably more than 5 wt %. If measured by addition amount, the amount of hydroiodic acid employed is preferably from 1 to 20 wt %, and more preferably from 2 to 10 wt %. The carbonylation can be carried out at a temperature of 100 to 220° C., and preferably 140 to 200° C.; and at a partial pressure of carbon monoxide of 10 to 80 atm, and preferably 10 to 50 atm.

Compared with the prior art the water content of the reaction medium for carbonylation should be maintained at a level of more than 14 wt % in order to increase the solubility of rhodium catalyst and attain the desirable catalyst activity, hydrohalic acid together with the catalyst promoter represented by formula (I) are used in the process of the present invention to thereby form a stable complex with the rhodium catalyst to prevent catalyst from being precipitated from the reaction medium when in a relatively low water content condition. In general, the catalyst promoter concentration is increased when the water content is decreased. When the catalyst promoter concentration is increased to a certain level, the rhodium catalyst in the reaction medium with low water content is allowed to maintain a concentration equivalent to that in the reaction system of the prior art with high water content. Consequently, the process of the present invention is capable of maintaining high reaction rate, enhancing space-time yield (STY), stabilizing rhodium catalyst stability and reducing catalyst precipitation under strict conditions of low carbon monoxide partial pressure and low water content. Also, the process of the present invention is capable of reducing purification cost.

EXAMPLES

The main apparatuses used in the process of the present invention include a reactor and a carbon monoxide storage tank. The reactor is equipped with a speed-variable motor to adjust speed to allow gas and liquid to be mixed therein well. The inner and outer shells of the reactor are, respectively, equipped with a serpentine condenser with cooling water and a heater such that a stable reaction temperature is attained. Pressure valves are mounted between the reactor and the carbon monoxide storage tank to control the pressure inside the reactor.

The tests for catalyst stability and reaction rate are performed by directly adding reactants to the mixed solution containing a rhodium catalyst, organohalide, water, hydrohalic acid and the catalyst promoter with the structure of formula (I) during the reaction. The reactor is kept at a pressure of 27 atm and at a temperature of 185° C., allowing the reaction to be carried out at a constant temperature and a constant pressure. At the initial stage of the reaction suitable quantities of reactants and monoxide are added with the ratio among them being adequately controlled, a small amount of esters is still present in the reaction medium after the reaction is completed to thereby improve and increase the catalyst instability such that the precipitation variation of the rhodium catalyst can be observed shortly.

During the reaction, a proper amount of reaction solution is collected from the sampling port for performing the analyses of iodine titration, gas chromatography and atomic absorption spectrometry. Rhodium precipitation is observed by referring to the analytical data, and the efficacy of hydrohalic acid associated with a catalyst promoter is measured. In the examples herein, all rhodium concentration data analyzed by atomic absorption spectrometer are obtained by standard assays for dissolved rhodium used in Monsanto procedures, and concentration unit is parts per million (ppm).

Examples 1-10 and Comparative Example 1

Improvement of the Carbonylation Rate (Reaction Productivity, Unit Space-Time Yield) by Adding Hydroiodic Acid Together with Various Catalyst Promoters 2% dicarbonyldiiodorhodium (15 g) solution was used. The composition of the reaction medium in the reactor is shown in Table 1, in which 4 wt % of hydroiodic acid was added and the remainder was acetic acid. Methanol was introduced into the reactor and reacted with carbon monoxide for 30 minutes. Then carbon monoxide consumption was recorded and the reaction solution was analyzed. The unit space-time yield (STY, mole/kg/hr) of acetic acid was measured. The results are shown in Table 1, wherein the comparative example was a blank test.

TABLE 1

| examples | catalyst promoters/metal (ppm) | water (wt %) | methyl iodide (wt %) | STY (mole/kg/hr) |
|---|---|---|---|---|
| example 1 | aluminium hydroxide | 10000 | 10 | 14 | 16.00 |
| example 2 | lead acetate | 10000 | 10 | 14 | 15.80 |
| example 3 | copper hydroxide | 10000 | 10 | 14 | 14.05 |
| example 4 | yttrium oxide | 10000 | 10 | 14 | 14.44 |
| example 5 | lanthanum chloride | 10000 | 10 | 14 | 14.83 |
| example 6 | zirconium hydroxide | 10000 | 10 | 14 | 16.58 |
| example 7 | vanadium oxide | 10000 | 10 | 14 | 14.24 |
| example 8 | molybdenum oxide | 10000 | 10 | 14 | 16.78 |
| example 9 | cerium oxide | 10000 | 10 | 14 | 14.24 |
| example 10 | ytterbium oxide | 10000 | 10 | 14 | 14.83 |
| comparative example 1 | — | | 10 | 14 | 13.65 |

In view of Table 1, the STY value of comparative example 1 is 13.65, and the STY values of examples 1-10, in which hydroiodic acid associated with 10000 ppm of different catalyst promoters were used, are all increased significantly. Particularly, aluminium, lead, zirconium, molybdenum etc. show better carbonylation efficacy. It is found that the use of the hydroiodic acid in combination with a catalyst promoter can effectively enhance methanol carbonylation rate.

Examples 11-14 and Comparative Example 2

Effect of the Use of the Hydroiodic Acid in Combination with Various Catalyst Promoters and Iodide Concentration on the Stabilization of Rhodium Catalyst Stability The same reaction steps of example 1 were repeated except that some different catalyst promoters were used. The content of water, methyl iodide and hydroiodic acid, and reaction conditions were the same as in example 1. After carbonylation, rhodium catalyst concentration (ppm) and iodide anion (I⁻) concentration (wt %) were measured and compared. The results are shown in Table 2.

TABLE 2

| examples | catalyst promoters/metal (ppm) | after carbonylation Rh(ppm) | I⁻ (wt %) |
|---|---|---|---|
| example 1 | aluminium hydroxide/10000 | 633 | 3.89 |
| example 4 | yttrium oxide/10000 | 532 | 2.32 |
| example 5 | lanthanum chloride/10000 | 700 | 1.48 |
| example 11 | zinc acetate/10000 | 462 | 3.70 |
| example 12 | cobalt acetate/10000 | 563 | 3.44 |
| example 13 | manganese acetate/10000 | 510 | 3.67 |
| example 14 | nickel acetate/10000 | 750 | 3.25 |
| comparative example2 | — | 450 | 0.74 |

In view of Table 2, compared with comparative example 2 using no catalyst promoter, all other examples that 4 wt % of hydroiodic acid was used in combination with 10000 ppm of the acetate salts of aluminium, yttrium, lanthanum, zinc, cobalt, manganese or nickel, reveal that the catalyst promoters can effectively stabilize iodide anion concentration and rhodium catalyst concentration in the reaction system, and the efficacy is dependent on the metal type. Therefore, the use of the hydroiodic acid associated with a catalyst promoter has substantial effects on maintaining iodide anion concentration and stabilizing rhodium catalyst, and further facilitates the carbonylation of methanol.

Examples 6, 8 and 15-18

Effect of Concentrations of Hydroiodic Acid and Catalyst Promoters on Carbonylation Rate (Reaction Productivity, STY)

The reaction steps of example 1 were repeated except that the concentrations of hydroiodic acid and catalyst promoters as shown in Table 3 were used, other components and reaction conditions were the same as in example 1. The STY values of acetic acid were calculated. The results are shown in Table 3.

TABLE 3

| examples | hydroiodic acid (wt %) | catalyst promoter | concentration as metal (ppm) | water (wt %) | STY (mole/kg/hr) |
|---|---|---|---|---|---|
| example 15 | 4 | molybdenum oxide | 5000 | 10 | 16.19 |
| example 8 | 4 | | 10000 | 10 | 16.78 |
| example 16 | 6 | | 15000 | 10 | 17.79 |
| example 17 | 4 | zirconium hydroxide | 5000 | 10 | 16.0 |
| example 6 | 4 | | 10000 | 10 | 16.58 |
| example 18 | 6 | | 15000 | 10 | 18.05 |

The results of Table 3 indicate that the STY values can be increased when the metal concentration of the catalyst promoter is increased from 5000 ppm to 10000 ppm under the condition of 4 wt % of hydroiodic acid (examples 8 and 15, examples 6 and 17). This shows that the increased amount of the catalyst promoter can enhance carbonylation. Furthermore, the STY value of carbonylation is further increased when the hydroiodic acid concentration is increased to 6 wt % and the metal concentration of catalyst promoter is increased to 15000 ppm (example 16 and 18). Consequently, the promotion of methanol carbonylation is even more obviously if the content of hydroiodic acid and the catalyst promoter can be increased simultaneously.

What is claimed is:

1. A process for preparing a carboxylic acid, comprising the steps of:
reacting an alcohol or its derivative with carbon monoxide in a liquid reaction solution to carry out a carbonylation reaction to form the carboxylic acid, wherein the liquid reaction solution comprises a rhodium catalyst, water, organohalide, carboxylic ester, hydrohalic acid, a catalyst promoter and the carboxylic acid, and wherein the catalyst promoter has a structure represented by formula (I):

$$M_n Y_z \quad (I)$$

wherein,
M is selected from the group consisting of group IIIA-IVA metals, group IB-VIIIB metals and lanthanides;
Y is selected from the group consisting of simple or complex anions of hydroxide, carbonate, oxalate, acetate, nitrate, oxygen-containing halic acid, sulfate, phosphate, halogen atom and oxygen atom; and
n and z are integers for balancing charges; and a dissolved concentration of the rhodium catalyst in the liquid reaction solution ranges from 200 to 5000 ppm.

2. The process of claim 1, wherein the alcohol is methanol and the carboxylic acid is acetic acid.

3. The process of claim 1, wherein the concentration of M in the catalyst promoter in the liquid reaction solution ranges from 5000 to 20000 ppm.

4. The process of claim 1, wherein the group IIIA-IVA metals comprise aluminum, tin and lead.

5. The process of claim 1, wherein the group IB-VIIIB metals comprise copper, zinc, yttrium, titanium, zirconium, vanadium, chromium, molybdenum, manganese, cobalt, nickel and palladium.

6. The process of claim 1, wherein the lanthanides comprise lanthanum, cerium and ytterbium.

7. The process of claim 1, wherein the hydrohalic acid is hydroiodic acid.

8. The process of claim 1, wherein the hydrohalic acid is added to the liquid reaction solution in an amount sufficient to provide the liquid reaction solution with iodide anions more than 3 wt % of the liquid reaction solution.

9. The process of claim 8, wherein the hydrohalic acid is added to the liquid reaction solution in an amount sufficient to provide the liquid reaction solution with iodide anions more than 5 wt % of the liquid reaction solution.

10. The process of claim 1, wherein the carboxylic ester is of an amount of 0.1 to 30 wt % of the liquid reaction solution.

11. The process of claim 10, wherein the carboxylic ester is of an amount of 0.1 to 5 wt % of the liquid reaction solution.

12. The process of claim 1, wherein the carboxylic ester is methyl acetate.

13. The process of claim 1, wherein the organohalide is of an amount of 5 to 30 wt % of the liquid reaction solution.

14. The process of claim 13, wherein the organohalide is of an amount of 10 to 30 wt % of the liquid reaction solution.

15. The process of claim 1, wherein the organohalide is methyl iodide.

16. The process of claim 1 wherein the water is of an amount of 1 to 14 wt % of the liquid reaction solution.

17. The process of claim 16, wherein the water is of an amount of 7 to 10 wt % of the liquid reaction solution.

18. A process for preparing a carboxylic acid, consisting of:
reacting an alcohol or its derivative with carbon monoxide in a liquid reaction solution to carry out a carbonylation reaction to form the carboxylic acid, wherein the liquid reaction solution consisting of a rhodium catalyst, water, organohalide, carboxylic ester, hydroiodic acid, a catalyst promoter and the carboxylic acid, and wherein the catalyst promoter has a structure represented by formula (I):

$$M_n Y_z \quad (I)$$

wherein, M is selected from the group consisting of group IIIA-IVA metals, group IB-VIIIB metals and lanthanides; Y is selected from the group consisting of simple or complex anions of hydroxide, carbonate, oxalate, acetate, nitrate, oxygen-containing halic acid, sulfate, phosphate, halogen atom and oxygen atom; and n and z are integers for balancing charges.

19. The process of claim 1, wherein a concentration of M in the catalyst promoter in the liquid reaction solution ranges from 100 to 50000 ppm.

20. The process of claim 7, wherein the hydrohalic acid is added to the liquid reaction solution in an amount sufficient to provide the liquid reaction solution with iodide anions more than 1 wt % of the liquid reaction solution.

* * * * *